United States Patent [19]
deBoisblanc

[11] Patent Number: 5,791,900
[45] Date of Patent: Aug. 11, 1998

[54] TEMPORARY TOOTH CONSTRUCTION

[76] Inventor: Robert J. deBoisblanc, 1322 Felicity St., New Orleans, La. 70130

[21] Appl. No.: 811,018

[22] Filed: Mar. 4, 1997

[51] Int. Cl.⁶ ............ A61C 13/12; A61C 13/225
[52] U.S. Cl. .......... 433/181; 433/178; 433/191; 433/202.1
[58] Field of Search .................. 433/178, 181, 433/182, 183, 191, 202.1

[56] References Cited

U.S. PATENT DOCUMENTS

| | | | |
|---|---|---|---|
| 1,412,224 | 4/1922 | Williams | 433/178 |
| 1,473,661 | 11/1923 | Baker | 433/178 X |
| 1,591,155 | 7/1926 | Craigo | 433/178 |
| 1,641,626 | 9/1927 | Eisenstein | 433/178 X |
| 2,350,196 | 5/1944 | Saffir | 433/191 |
| 2,722,053 | 11/1955 | Moyer | 32/5 |
| 3,153,855 | 10/1964 | Holland | 433/178 X |
| 3,267,574 | 8/1966 | Oddo, Jr. | 32/5 |
| 3,530,582 | 9/1970 | Weissman | 433/191 X |
| 4,060,898 | 12/1977 | Orthwein | 32/40 R |
| 4,661,068 | 4/1987 | Harrison et al. | 433/181 |
| 4,950,135 | 8/1990 | Korber et al. | 433/180 |
| 5,458,489 | 10/1995 | Tenhyson | 433/191 X |

*Primary Examiner*—Nicholas D. Lucchesi
*Attorney, Agent, or Firm*—Henderson & Sturm

[57] ABSTRACT

A temporary tooth construction 10 for attachment to portions of permanent teeth 101, 102 on opposite sides of a gap formed by at least one missing tooth. The temporary tooth construction 10 includes a tooth members 20 provided with a pair of anchor member 30 on opposite sides of the tooth member 20 wherein each anchor member 30 releasably engages portions of the permanent teeth 101, 102 on opposite sides of a gap formed by a missing tooth.

2 Claims, 2 Drawing Sheets

TEMPORARY TOOTH CONSTRUCTION

CROSS-REFERENCE TO RELATED APPLICATIONS

Not Applicable.

STATEMENT REGARDING FEDERALLY SPONSORED RESEARCH OR DEVELOPMENT

Not Applicable.

AUTHORIZATION PURSUANT TO 37 C.F.R. §1.71 (d) (e)

A portion of the disclosure of this patent document, including appendices, may contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to orthodontic devices and more particularly to a temporary tooth construction which is anchored to adjacent permanent teeth disposed opposite a gap formed by at least one missing tooth.

2. Description of the Related Art

As can be seen by reference to the following U.S. Pat. Nos. 2,722,053; 3,267,574; 4,060,898; and 4,950,162; the prior art is replete with myriad and diverse dental restorative devices.

While all of the aforementioned prior art constructions are more than adequate for the basic purpose and function for which they have been specifically designed, these patented arrangements are neither designed nor intended to fulfill the role provided by the subject matter of the instant invention.

Due to the exorbitant cost of most permanent tooth replacement devices, many individuals having limited or fixed incomes and/or not being covered by comprehensive dental insurance have sought out stop gap or temporary tooth constructions that will not only maintain their usual physical appearance, but will also serve for at least a reasonably period of time as an adequate replacement for the more costly permanent solution to the problem.

As a consequence of the foregoing situation, there has existed a long standing need among many individuals for a low cost yet simple, efficient and aesthetically pleasing temporary tooth construction that will serve at least one a limited time basis as an adequate substitute for a more permanent tooth replacement.

Those concerned with these and other problems recognize the need for an improved temporary tooth construction.

BRIEF SUMMARY OF THE INVENTION

The present invention discloses a temporary tooth construction that forms the basis of the present invention. The invention comprises a tooth unit designed, dimensioned, and configured to present the external appearance of one or more of a user's teeth, and a plurality of anchor units which operatively engage the opposite sides of the tooth unit, as well as releasably engage portions of the user's existing teeth which are disposed adjacent the opposite sides of the tooth unit.

2

As will be explained in greater detail further on in the specification, each of the anchor units comprises a generally resilient, yet semi-rigid anchor member having a generally cylindrical post element dimensioned to engage a complementary bore in the tooth unit, and a generally C-shaped capture element dimensioned to resiliently engage a portion of an existing tooth surface.

Therefore, an object of the present invention is the provision of an improved temporary tooth construction.

BRIEF DESCRIPTION OF THE SEVERAL VIEWS OF THE DRAWINGS

Other objects, advantages, and novel features of the present invention will become apparent from the following detailed description of the invention when considered in conjunction with the accompanying drawings, wherein.

DETAILED DESCRIPTION OF THE INVENTION

Figure 1:
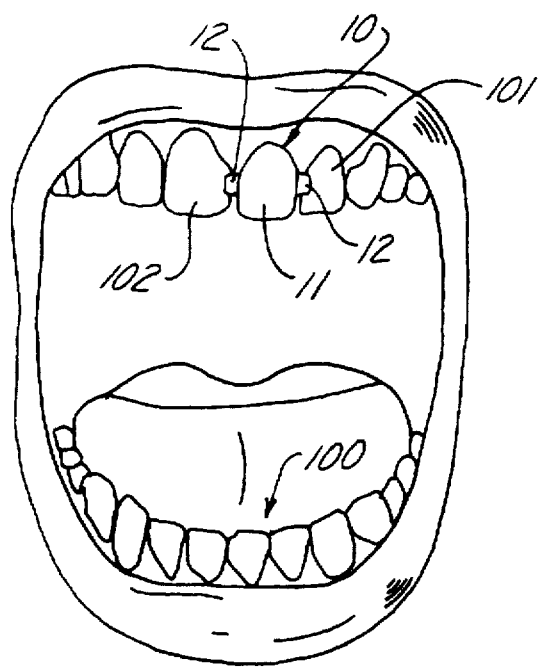
FIG. 1 is a perspective view of the temporary tooth construction that forms the basis of the present invention installed in a user's mouth.
Figure 3:
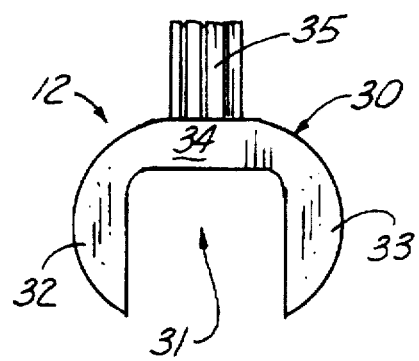
FIG. 3 is a top plan view of the temporary tooth construction anchor element.

Referring now to the drawings, wherein like reference numerals designate identical or corresponding parts throughout the several views, FIG. 1 shows the invention depicted generally at 10. The construction 10 comprises in general a tooth unit 11 and a pair of anchor units 12. These units will now be described in seriatim fashion.

In the first version of the preferred embodiment illustrated in FIG. 2, the tooth unit 11 comprises a single temporary tooth member 20 having a front face portion 21, which is configured in the shape of a human tooth and a peripheral edge portion 22 which is provided with a pair of diametrically opposed generally cylindrical bores 23 whose purpose and function will be described presently.

Turning now to FIGS. 3 through 7, it can be seen that each of the pair anchor units 12 are identical and comprise a contoured anchor member 30 having an enlarged generally C-shaped capture element 31, including a pair of side walls 32, 33, and a base portion 34, and a centrally disposed post element 35 extending rearwardly from the base portion 34 of the capture element 31 and provided with a plurality of fluted grooves 37.

In the preferred embodiment of this invention, the anchor members 30 are fabricated from a clear, semi-rigid, yet semi-flexible plastic material. The central post element 35 is dimensioned to be engaged in one of the cylindrical bores 23 in the tooth member 20 and the side walls 32, 33 of the capture element 31 are dimensioned to resiliently engage the periphery of one of the permanent teeth 101, 102 etc., in the user's mouth 100 to maintain the temporary tooth construction in the desired location.

Figure 2:
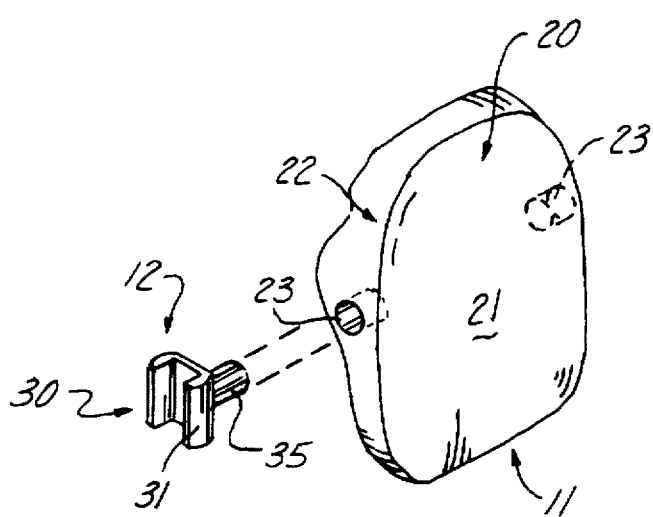
FIG. 2 is an exploded perspective view of the temporary tooth construction.
Figure 4:
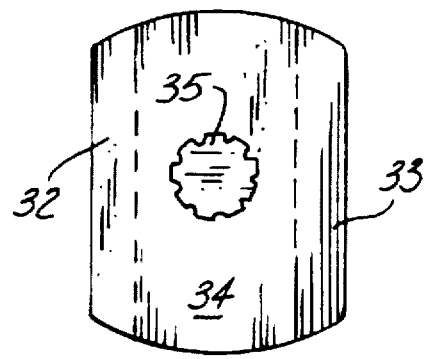
FIG. 4 is a front plan view of the temporary tooth construction anchor element.
Figure 5:
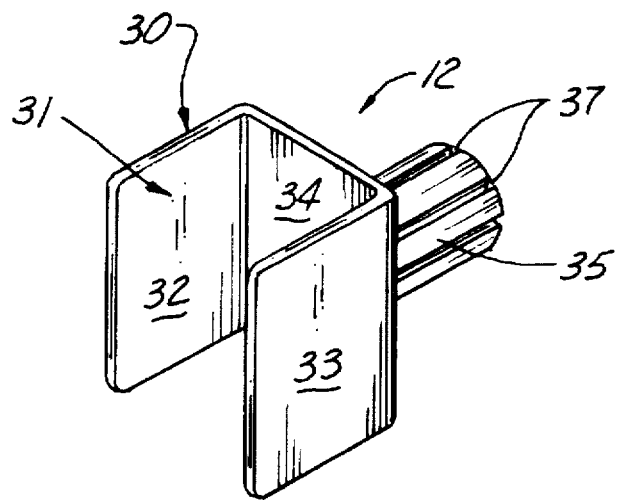
FIG. 5 is an enlarged perspective view of the anchor element.

In the single tooth version of the preferred embodiment illustrated in FIGS. 1 and 2, the capture element 31 on the opposite sides of the single tooth member 20 slidably engage the adjacent peripheral portions of the adjacent permanent teeth 101 and 102 to maintain the temporary tooth construction in place.

Figure 6:
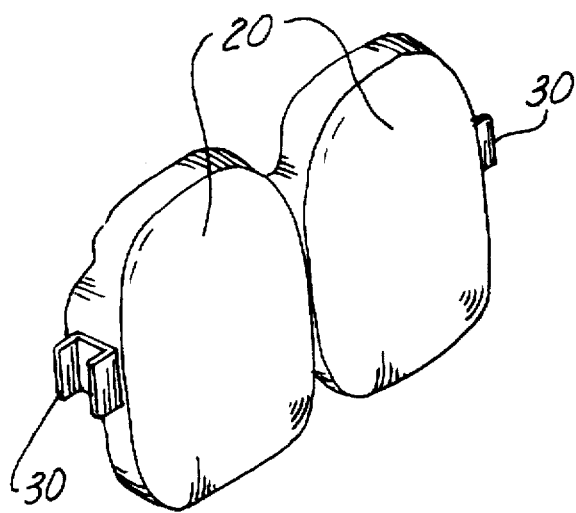
FIG. 6 is a perspective view of the multi-toothed version of the invention.
Figure 7:
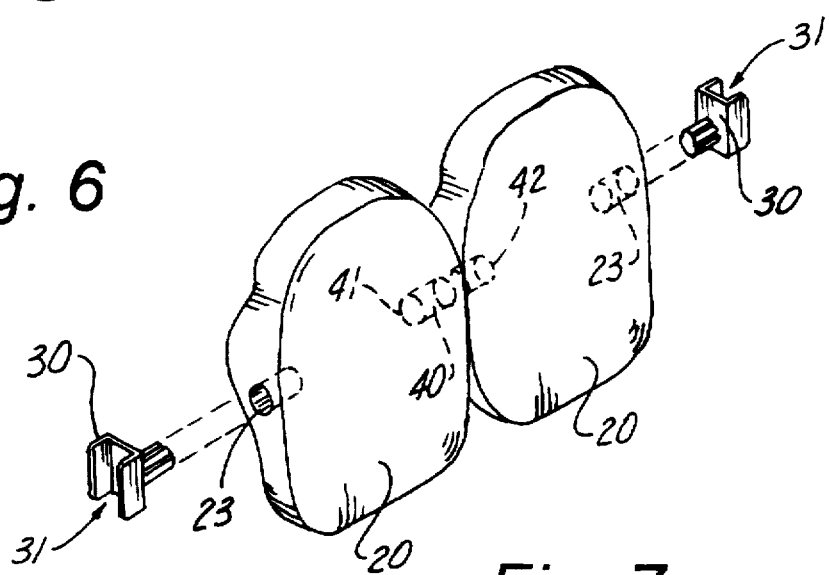
FIG. 7 is an exploded perspective view of the multi-toothed version.

Turning now to FIGS. 6 and 7, it can be seen that in the multi-toothed version of the preferred embodiment, a pair of tooth members 20, 20 are joined together by an elongated cylindrical connector member 40 whose opposite ends 41, 42 are dimensioned to be received in the opposed bore holes 23 in the adjacent tooth members 20, 20.

As was the case with the single tooth version, the capture elements 31 of the anchor members 30 will slidably engage adjacent permanent tooth portions to maintain the temporary tooth construction in place.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

What is claimed is:

1. A temporary tooth construction for releasable attachment to adjacent permanent teeth portions on opposite sides of a gap formed by at least one missing tooth in a user's mouth the temporary tooth construction consisting of:

at least one tooth unit including a tooth member having a front face portion configured in the shape of a human tooth and a peripheral edge portion;

anchor means associated with opposite sides of the peripheral edge portion for releasably engaging the temporary tooth construction to portions of the permanent teeth portions on the opposite sides of said gap wherein said tooth member is provided with a pair of diametrically aligned bores dimensioned to receive a portion of said anchor means, said anchor means comprising a pair of identical anchor members, and each anchor member is fabricated from a clear semi-rigid, yet semi-flexible plastic material and includes a generally C-shaped capture element and a rearwardly facing cylindrical post element wherein the capture element includes a pair of side walls and a base portion, the cylindrical post element projects rearwardly from the base portion and is dimensioned to be received in one of the aligned bores in the tooth member; and said cylindrical post element is provided with a fluted periphery.

2. The temporary tooth construction as in claim 1 further comprising:

at least one additional tooth unit including a tooth member having a front face portion and a peripheral edge portion; and a connector member for joining said at least one tooth unit and said at least one additional tooth unit to one another.

* * * * *